United States Patent
Odermatt

[19]
[11] Patent Number: 5,871,089
[45] Date of Patent: Feb. 16, 1999

[54] MULTITHREAD PACKAGE FOR SURGICAL SEWING MATERIAL

[75] Inventor: Erich K. Odermatt, Rubi, Spain

[73] Assignee: B. Braun Surgical AG, Switzerland

[21] Appl. No.: 912,777

[22] Filed: Aug. 18, 1997

[30] Foreign Application Priority Data

Aug. 28, 1996 [DE] Germany .................. 196 34 726.2

[51] Int. Cl.⁶ .................................................. A61B 17/06
[52] U.S. Cl. .......................... 206/63.3; 206/227; 206/380
[58] Field of Search .................. 206/63.3, 227, 206/380, 382

[56] References Cited

U.S. PATENT DOCUMENTS

| | | | |
|---|---|---|---|
| 3,857,484 | 12/1974 | Thyen | 206/227 |
| 3,985,227 | 10/1976 | Thyen et al. | 206/63.3 |
| 4,135,623 | 1/1979 | Thyen | 206/63.3 |
| 4,391,365 | 7/1983 | Batchelor | 206/63.3 |
| 4,572,363 | 2/1986 | Alpern . | |
| 5,101,968 | 4/1992 | Henderson et al. | 206/63.3 |
| 5,236,082 | 8/1993 | Brown | 206/63.3 |
| 5,435,438 | 7/1995 | Scanlon | 206/63.3 |
| 5,494,154 | 2/1996 | Ainsworth et al. | 206/63.3 |
| 5,529,175 | 6/1996 | Brunken | 206/63.3 |
| 5,582,288 | 12/1996 | Zatarga | 206/63.3 |

FOREIGN PATENT DOCUMENTS

| | | |
|---|---|---|
| 0065098 | 3/1982 | European Pat. Off. . |
| 0505612 | 11/1991 | European Pat. Off. . |

OTHER PUBLICATIONS

EP Search Report of EP 97 11 3653 dated Nov. 14, 1997.

*Primary Examiner*—Byron P. Gehman
*Attorney, Agent, or Firm*—Diller, Ramik & Wight, PC

[57] ABSTRACT

The package (10) provides a first panel (11) and a second panel (12) foldably connected thereto. The first panel (11) serves as a winding panel and is connected at opposite sides to various separation panels (18,19, 20,21). Thread coils (42) can be wound on the first panel (11), the needles (43) thereof are inserted into a foam material needle support (24). After that, a separation panel (19) is folded over to cover a part of the finished thread coil (42). Above that, a further thread coil is produced. The individual separation panels (18–21) each only cover a part of the thread coil below, yet keep the threads from becoming entangled with one another.

11 Claims, 8 Drawing Sheets

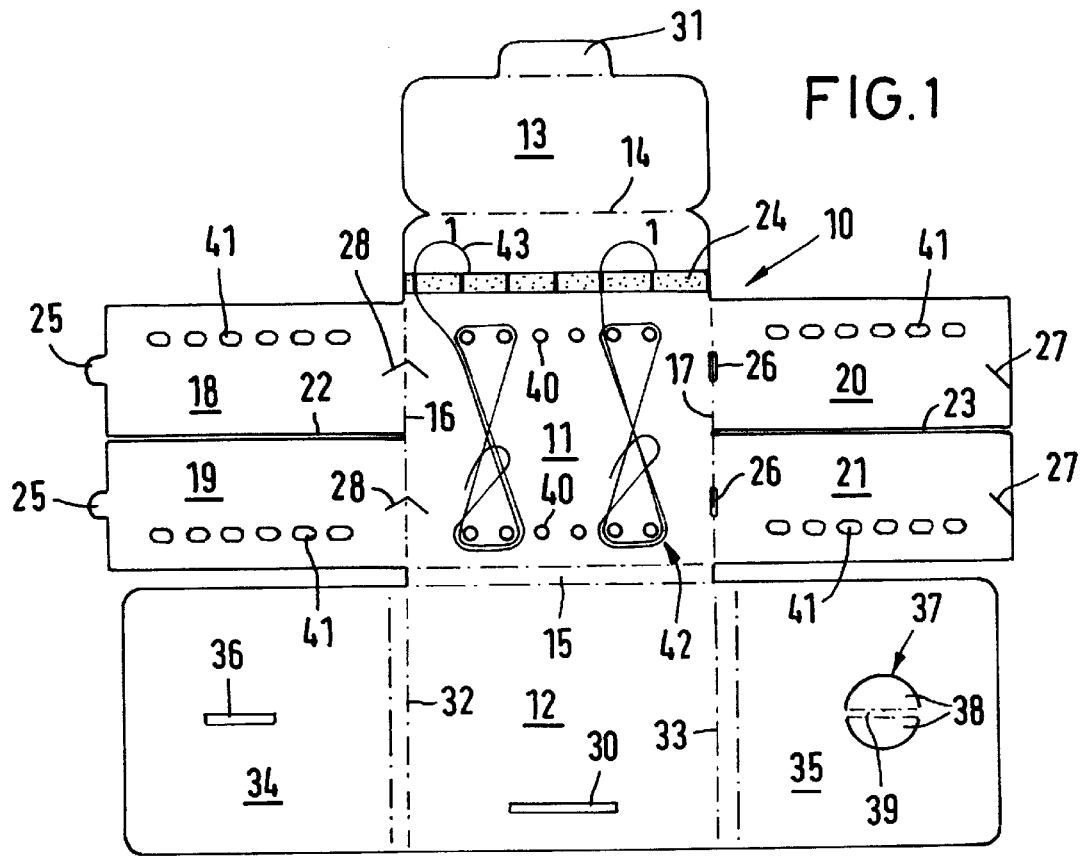
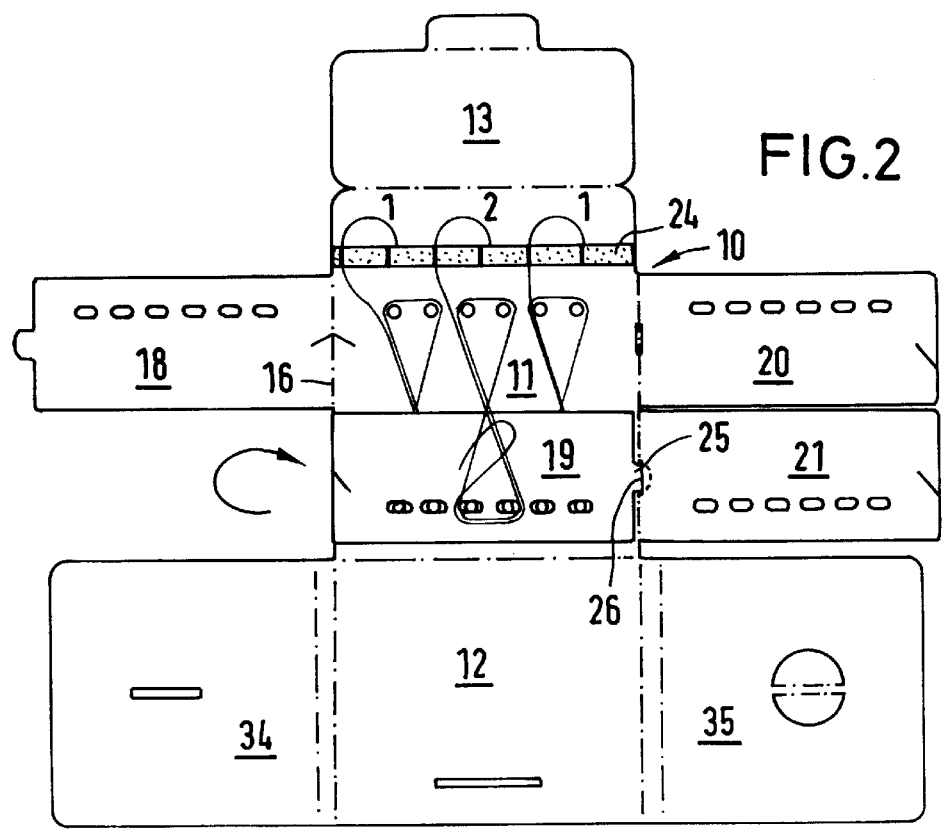

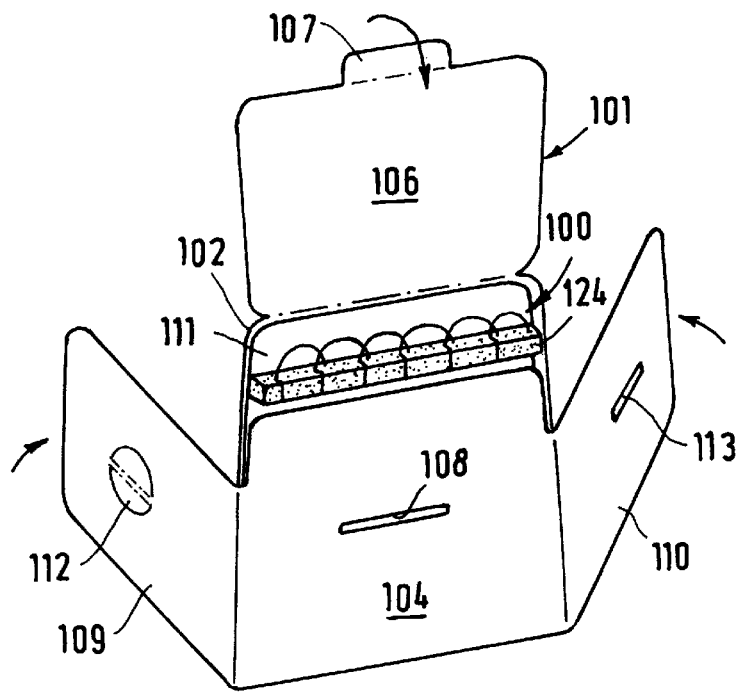
FIG. 20
FIG. 21
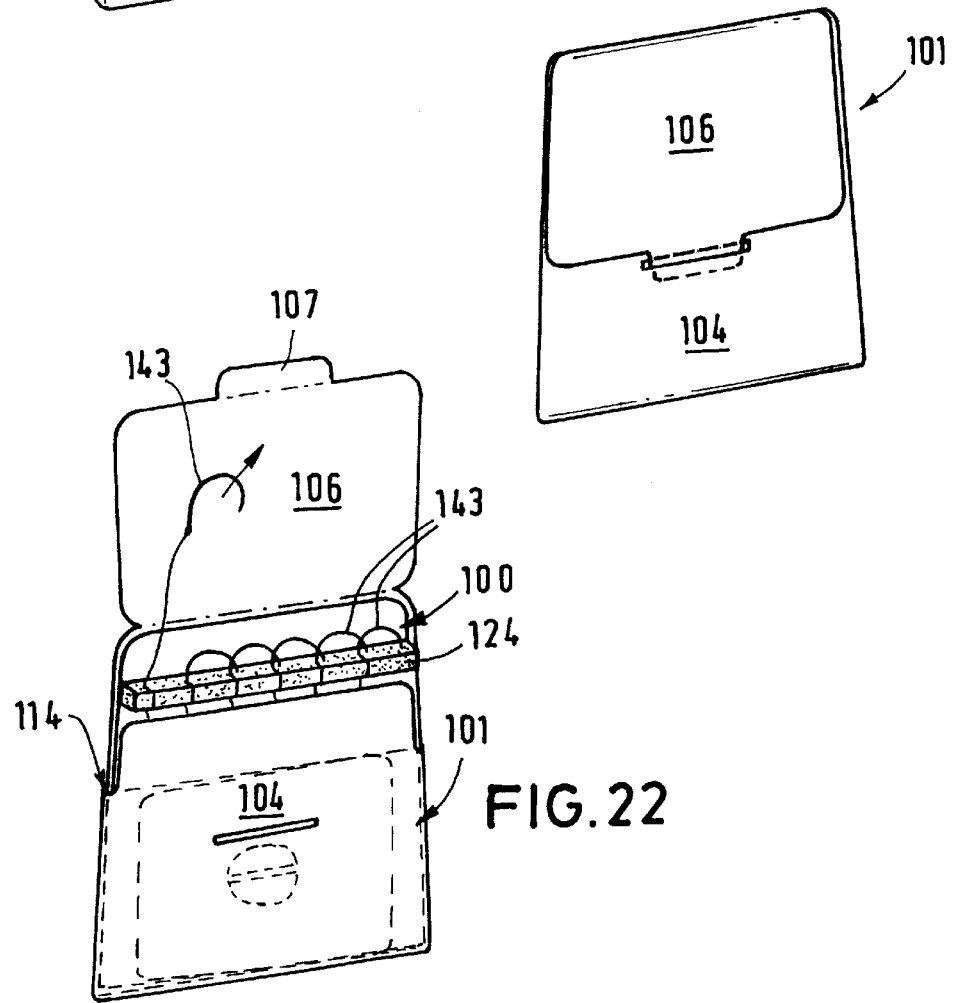
FIG. 22

MULTITHREAD PACKAGE FOR SURGICAL SEWING MATERIAL

BACKGROUND OF THE INVENTION

The present invention refers to a multithread package for surgical sewing material, containing multiple threads each connected to at least one needle.

From EP 0 065 098 B1, there has been known a multithread package for surgical sewing material comprising a folded card forming the cover of the package. A first panel of the folded card serves as a winding panel. This panel has multiple holes wherethrough pins can be placed around which a thread is being wound. Furthermore, there is attached to the winding panel a needle supporting means in the form of a strip of foam material with multiple slots. The needles attached to the threads can be individually inserted into the slots. After the first thread has been wound on the first panel, a separation panel is put on the first panel so that the wound thread is covered. This separation panel also comprises holes, which are aligned with those of the first panel, so that the winding pins can be placed therethrough. A further thread is then placed on the separation panel by being wound around the winding pins. After that, further separation panels can be put on top. The stack of separation panels with the thread coils in between is then covered by further panels, which are folded over, forming a container together with the first panel. The needles of all the threads are held in place by the needle supporting means. Additionally, a separate sewing material support with a needle supporting means of its own can be inserted into the envelope, which support presents a package of further needles after the envelope has been opened. Instead of using the stack of separate separation panels, a structure of interconnected separation panels in the shape of an accordion can be employed. In any case, the separation panels are additional parts which have to be attached to the card structure, causing the package to become very thick.

EP 0 506 612 B1 discloses a multithread package of multiple panels arranged side by side and forming a complex folding package and comprising lateral recesses for winding pins. A thread can be wound on any panel and can then be covered by folding over an adjacent panel. Then another thread is wound on the adjacent panel. The needles of all the threads are collected in a needle supporting means foldably connected to the first winding panel. The needles are inserted into a window of the second panel so that they can later be grasped from the outside. The needles are therefore not completely exposed to be grasped, but only on their needle portions projecting from the window.

SUMMARY OF THE INVENTION

The invention is based on the objective to provide a multithread package for surgical sewing material able to accommodate a large number of threads using little package material without the threads becoming entangled, and which makes it possible to grasp the needles in a simple manner.

The multithread package according to the invention comprises a first panel serving as a winding panel or base panel connected, at opposing edges thereof, with separation panels which can be folded over the first panel. In this manner, multiple threads can be wound and laid down on the first panel one after another, which threads can then be covered by folding over one of the separation panels, the next thread being wound over this separation panel. The separation panels can be folded over the first panel alternately from the right and from the left. This package can be inserted into an envelope either connected thereto or separate.

According to a preferred embodiment of the invention, there are provided at least two separation panels at each of the two opposing edges of the first panel, at least two opposing separation panels being folded over each other on the first panel in each case. This is based on the consideration that it is not necessary for each separation panel to cover the first panel completely. Rather, it is sufficient for one separation panel to cover just a part of the first panel and for another separation panel to cover a further part of the first panel. Thus, the sewing material covered by a separation panel can be held in place in a defined manner, while another thread is being wound over the separation panel. It is sufficient to cover just a part of the thread coil by the separation panel without incurring the danger of the exposed part of the thread coil becoming entangled with one of the adjacent thread coils. This is how it is achieved to save a considerable amount of panel material.

In another embodiment of the invention, the separation panels extend across parts of the width of the first panel, for example half the width, and each separation panel is connected to a backfolding panel. In this context, a thread coil can be laid down under each separation panel and above the same separation panel (but under the backfolding panel). The separation panels form an envelope with the first panel on the one hand and the backfolding panel receiving a thread coil on the other hand.

It is possible to form the multithread package in such a way that the first panel is integrally connected to an integrated envelope. For this purpose, the first panel is connected to a second panel, which can be folded over the separation panels folded on the first panel.

Alternatively, it is possible to provide an additional envelope with a separate blank, which is inserted into the package as a sewing material carrier. After the envelope has been opened, the needle supporting means of the package is exposed. The package can be inserted into the envelope loosely or secured thereto. According to a preferred embodiment of the invention, both the envelope and the package are trapezoid in shape, the width thereof decreasing towards the envelope opening. As a result, the package is held in place in the envelope and cannot be extracted through the envelope opening. To take out the threads, it is necessary only to open a cover panel in order to expose the envelope opening and the needle supporting means, thus making them accessible.

BRIEF DESCRIPTION OF THE DRAWINGS

Embodiments of the invention will now be described in greater detail with reference to the drawings.

FIG. 1 shows the blank of a multithread package in an open state after two thread coils have been produced, FIG. 2 shows the package of FIG. 1 after a separation panel has been folded back and a second thread coil has been produced on this separation panel, FIG. 20 shows the envelope being closed, with an inserted sewing material carrier, FIG. 21 shows the package in a closed state, and FIG. 22 shows a thread being taken out of the envelope, the cover panel of which has been opened.

DESCRIPTION OF THE PREFERRED EMBODIMENTS

Figure 3:
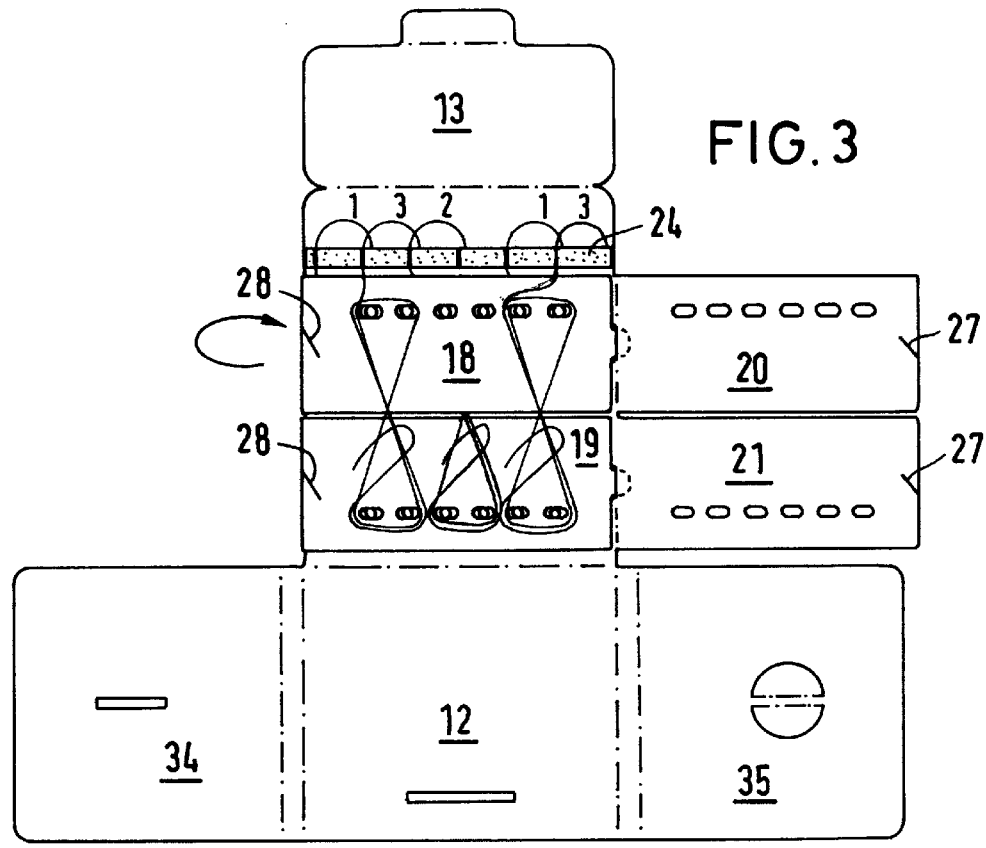
FIG. 3 shows the same package after a second separation panel has been folded back and two third thread coils have been produced.

The multithread package 10 of the embodiment of FIGS. 1–8 consists of an integral carton blank with a rectangular first panel 11, the longitudinal edge thereof bordering on a rectangular second panel 12. Opposite the second panel 12 is a cover panel 13, which can be folded around a folding line 14. The second panel 12 is connected to the first panel 11 by a transverse strip 15 defined by two folding lines. The first panel 11, the second panel 12 and the cover panel 13 are each of the same width at the folding lines and form a longitudinal strip of material.

The first panel 11 laterally borders on longitudinal folding lines 16,17. The folding line 16 borders on two separation panels 18,19, and the folding line 17 also borders on two separation panels 20,21. Each of these separation panels has a width substantially similar to the one of the first panel 11. The separation panels 18,19 are separated from each other by a transverse slot 22 and the separation panels 20,21 are also separated from each other by a transverse slot 23. The separation panels 18 and 20 can be folded over each other above the upper area of the first panel 11 and the separation panels 19 and 21 can be folded over each other on the lower area of the first panel 11.

Above the area of the first panel 11 which can be covered by the separation panels 18–21 there is a needle supporting means 24 in the form of a strip of foam material providing multiple transverse or slant slots, into which the needles of sewing material threads can be inserted in order to secure the needles thereto.

At the edges of the separation panels 18,19 opposite the first panel 11 there are tabs 25, which can be inserted into slots 26 provided along the opposite folding line 17 in order to secure the separation panels 18,19 in the closed state.

The panels 20,21 have, at the outmost longitudinal edges thereof, transverse slots 17, which can engage with the slots 28 in the shape of an inverted V at the folding line 16 in order to secure the separation panels 20,21 in the closed state.

The second panel 12 is provided with an insertion slot 30, into which a tab 31 of the cover panel 13 can be inserted in order to secure the package in the closed state.

The second panel 12 is defined by longitudinal folding lines 32, 33, each bordering on closing panels 34 and 35, respectively. The closing panels 34 have a transverse slot 36, and the closing panel 35 is provided with a locking element 37, which can be placed through the transverse slot 36 and locked behind it. This locking element 37 consists of two semicircular flaps 38 arranged at both sides of a web 39 and able to be folded around the web 39. In the state of being folded out, the flaps 38 are adjacent each other and can be placed through the slot 36. Two, in this case transverse, rows of holes 40 are provided for the insertion of the winding pins. Each of the separation panels 18–21 also comprises a row of holes 41. When the separation panel has been folded around the folding line 16 or 17, respectively, onto the first panel 11, the holes 41 of the separation panel aligned to be congruent with the holes 40 of the first panel 11. The holes 41 are formed as elongated holes having the greatest length thereof in a transverse direction, so that the process of folding back is not impaired by the winding pins.

The folding card spread out according to FIG. 1 is put on a group of winding pins extending through the holes 40. Then the thread coils 42 are wound out of surgical thread material, by machine or manually. In the present case, a coil in the shape of an 8 is provided, however, coils in the shape of an 0 or in a meander shape can also be produced. Each coil of sewing material has at least one bow-shaped needle 43 secured to the thread. This needle 43 is fixed to the needle supporting means 43 consisting of foam material such that it can be grasped manually or by an instrument at a later time to extract the corresponding thread from the package.

In FIGS. 1–4, the thread coils 42 are each designated, in the order of their production, by numbers 1 to 4.

According to FIG. 1, two first thread coils 1 are directly wound on the first panel 11. In order not to obstruct each other, these thread coils are provided at a distance from each other. Each loop of a thread coil is wound around two holes or two winding pins placed through the holes 40, two holes 40 remaining unused between the two thread loops, so that the thread loops are provided at the required distance from each other.

After the production of the first thread loop 1, one of the panels 18,19, in the present case the separation panel 19, is folded around the folding line 16 over the lower area of the first panel 11, the tab 25 being placed through the slot 26. In this manner, the separation panel 19 covers the lower halves of the first thread coils 1 already produced. Then a second thread coil 2 is wound between the first thread coils 1 in an area which is still free between the first thread coils 1. The needles 32 of all the thread coils are secured to the same needle supporting means 24.

After the production of the second thread coil 2, the upper left separation panel 18 is folded back such as to cover the upper halves of the (three) thread coils already produced. Then, according to FIG. 3, two (third) thread coils 3 are being wound over the two separation panels 18, 19, exactly above the two first thread coils 1. On the lower separation panel 19, the third thread coils 3 do not obstruct the second thread coil 2, as half of this coil is already secured below the upper separation panel 18. The third thread coils 3 are provided at a distance from each other and also do not obstruct each other.

Figure 4:
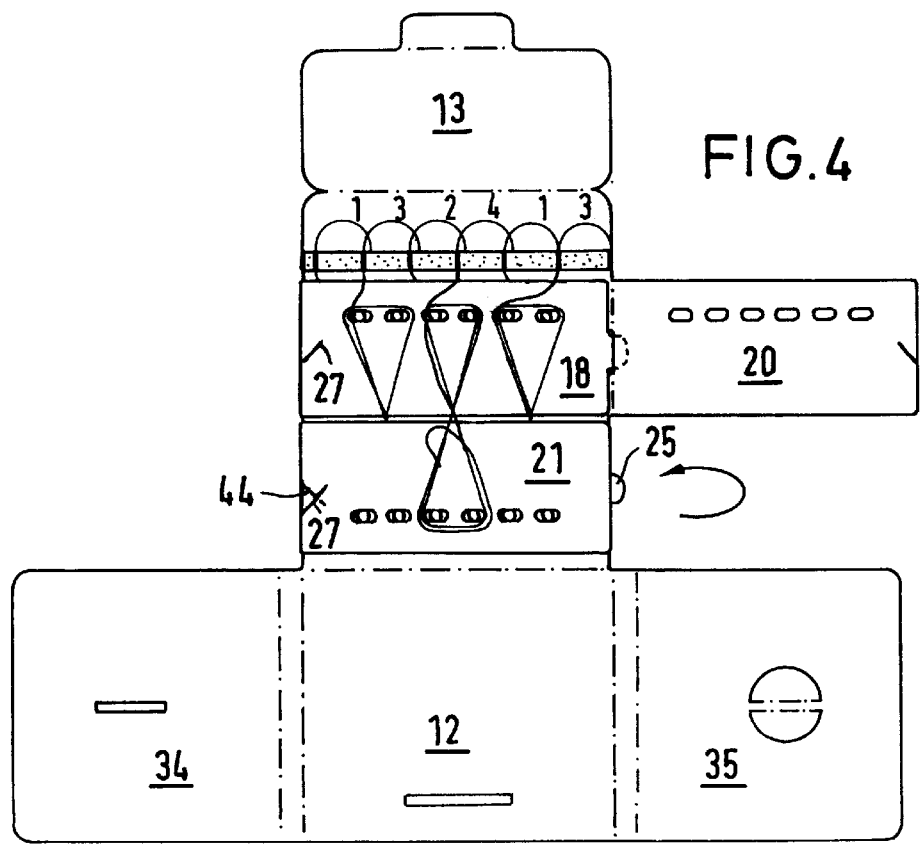
FIG. 4 shows the package after a third separation panel has been folded back and a fourth thread coil has been produced.
Figure 5:
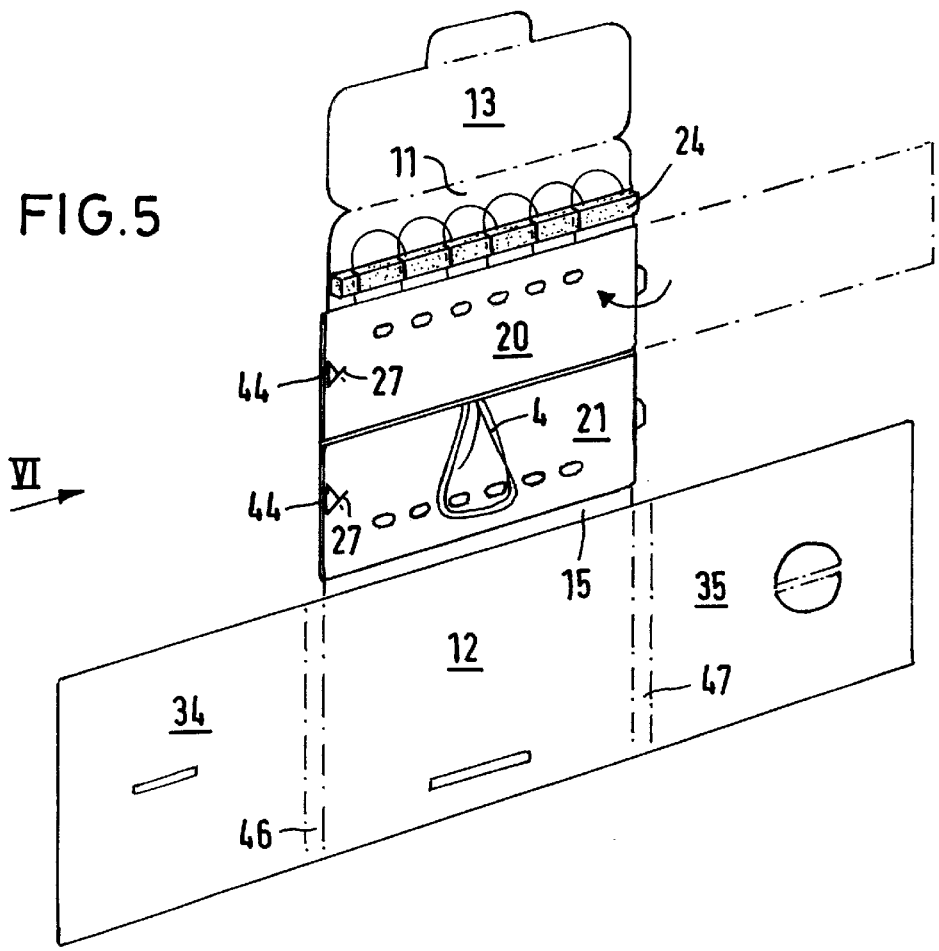
FIG. 5 shows the package after the fourth separation panel has been folded over (closed)

After that, according to FIG. 4, the right lower separation panel 21 is folded on the left lower separation panel 19 and secured by the tip 44 formed by the slot 28 in the shape of a V being placed through the transverse slot 27 of the separation panel 21. Now a fourth thread coil 4 is laid down on the panels 18,21, between the two third thread coils 3. The last separation panel 20 covers the upper part of the fourth thread coil 4. It is locked with the transverse slot 27 thereof behind the tip 44 formed by the dual slot 28.

Figure 7:
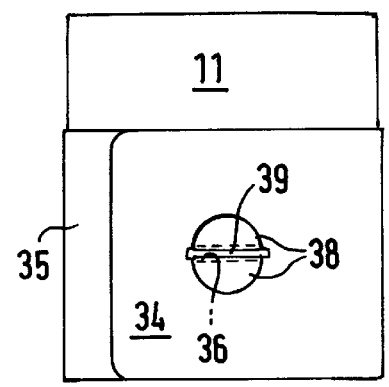
FIG. 7 shows a face view of the nearly closed package with an extractable second layer.

After all the thread coils have been put into place and secured, the winding pins are extracted from the holes 40,41, and further sewing material carriers 45 described later can be placed in front of the first panel 11 with the separation panels folded over it. Then the second panel 12 is folded over the further sewing material carrier 45 (FIG. 7). It can be seen that the second panel 12 leaves exposed the needle supporting means 24 provided in the first panel 11.

Figures 8, 9:
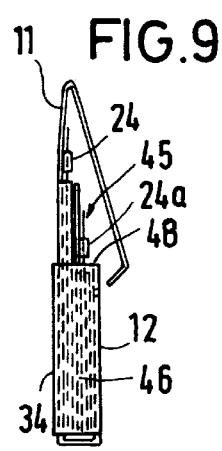
FIG. 8 shows a back view of the package according to FIG. 7 from the viewing direction of arrow VIII.
FIG. 9 shows a face view similar to the one of FIG. 7 in another embodiment presenting two rows of needles.

As a next step, the closing panel 35 is folded behind the first panel 11, and the closing panel 34 is folded behind the closing panel 35, the two wings 38 being placed through the slot 36 and then folded apart. FIG. 8 shows the back side of the package, the closing panel 34 forming the outer wall. All the panels 11,34,35 represented from the front side in FIG. 1 are visible from the back side in FIG. 8.

Figure 6:
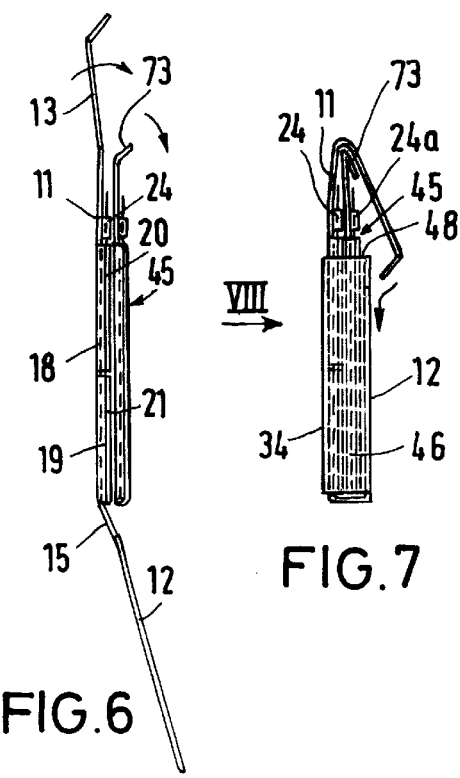
FIG. 6 shows a face view of the package according to FIG. 5 from the viewing direction of arrow VI, with an extractable second layer.

The closing panels 34,35 are connected to the second panel 12 by webs 46,47 which are defined, similarly to the web 15, by folding lines or incisions. When the second panel 12 is folded over the first panel 11 and the closing panels 34,35 are interlocked at the back side of the package, an envelope 48 is formed between the panels 11,12 wherein the additional sewing material carrier 45 is inserted. In FIGS. 6 and 7, the layer 45 of sewing material can be extracted by means of the tab 73.

FIG. 9 represents a different embodiment in the same view as FIG. 7, with the second panel 12 being shorter than in the case of the first embodiment, so that it does not extend close to the needle supporting means 24 in the backfolded state, but ends a considerable way before. This sewing material carrier 45 comprises a needle supporting means 24a of its own and ends below the needle supporting means 24 of the package. Therefore, the two needle supporting means 24,24a are exposed such that the sewing material carrier 45 does not have to be extracted to provide access to the needles of the sewing material carrier 24, i. e., both rows of needles are presented.

Figure 10:
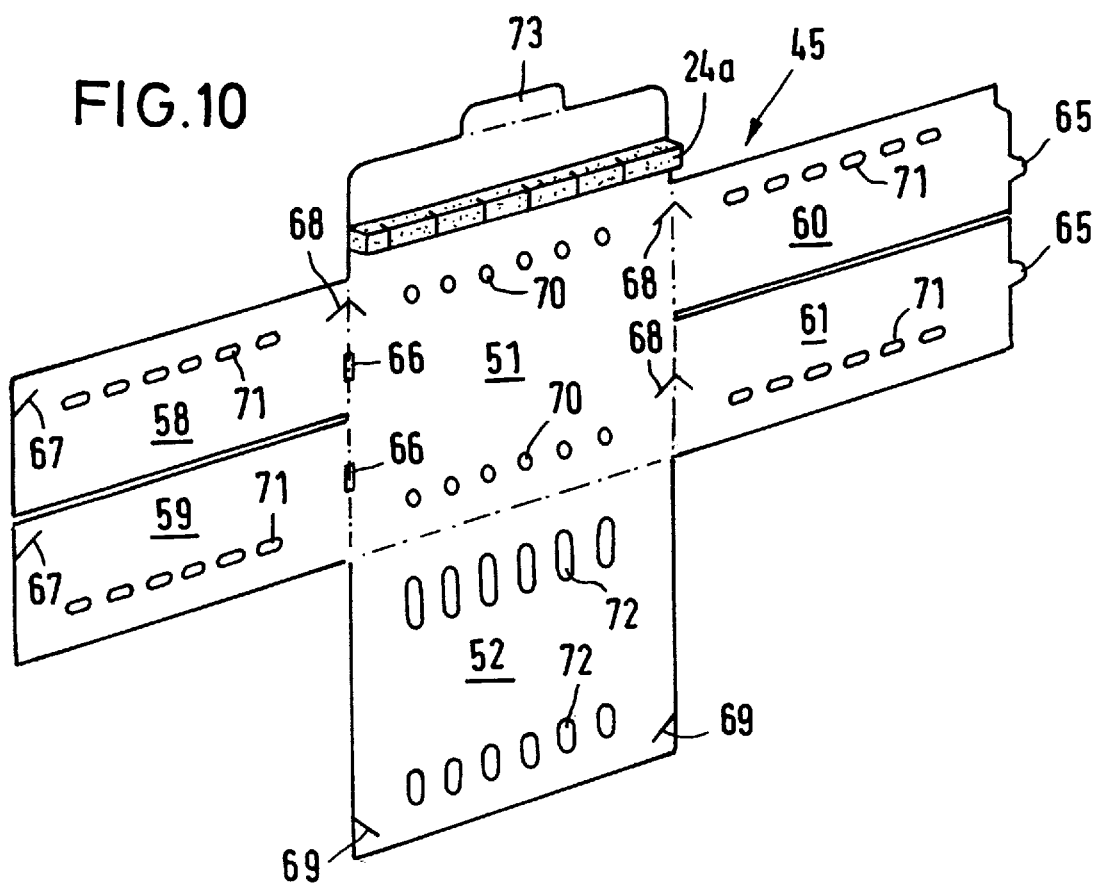
FIG. 10 shows the blank of a separate sewing material carrier.
Figure 11:
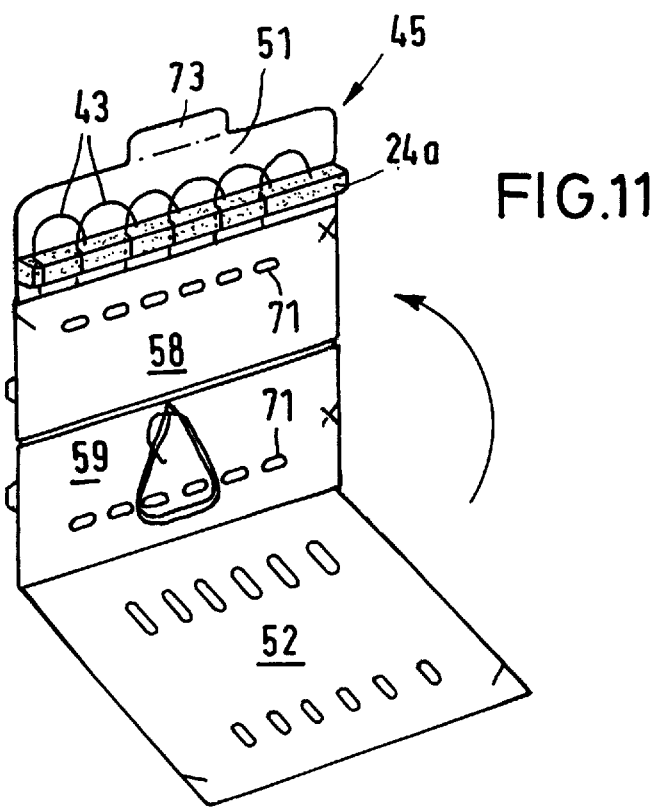
FIG. 11 shows the further sewing material carrier being closed.
Figure 12:
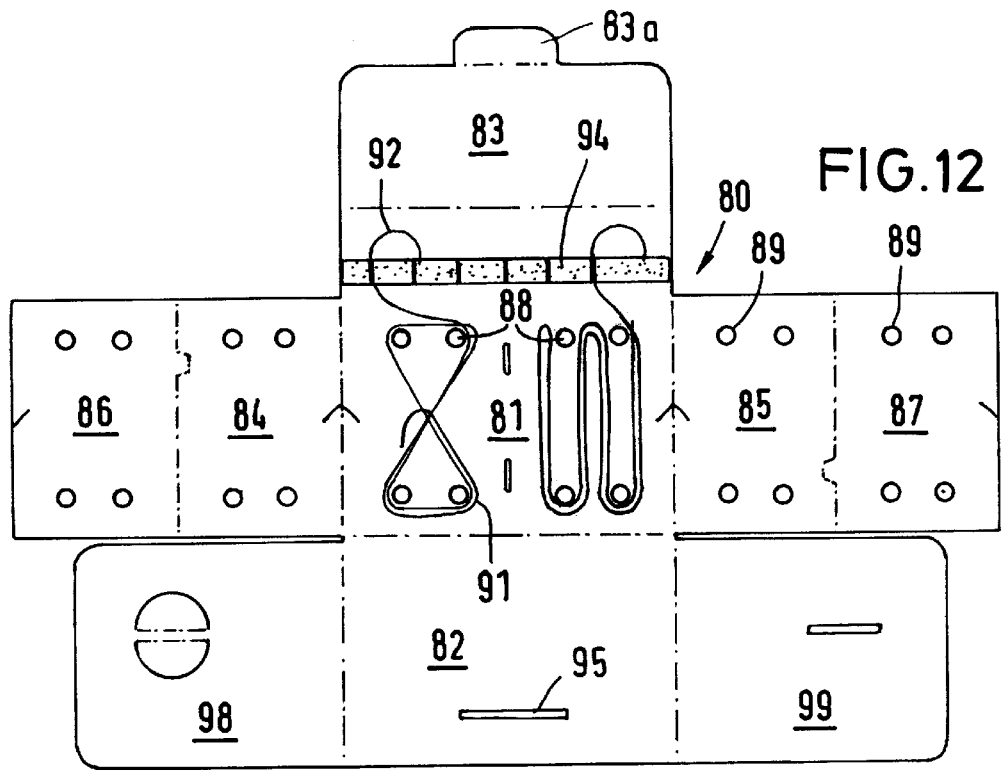
FIG. 12 shows another embodiment of the package after two first thread coils in the shape of an 8 and in a meander shape have been produced.
Figure 13:
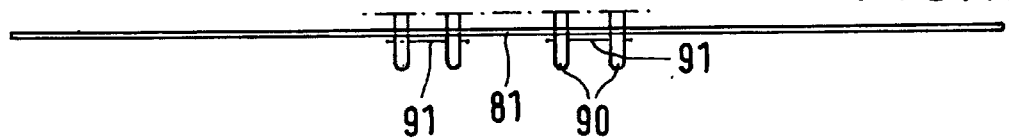
FIG. 13 shows a face view of the package according to FIG. 12 with inserted winding pins.

In FIGS. 9–11, the additional sewing material carrier 45 inserted into the envelope 48 of the package is represented. It also comprises a first panel 51 and a second panel 52 foldable over the first panel. Laterally next to the first panel 51 are arranged two separation panels 58,59 and 60,61, respectively. Two rows of holes 70 are provided in the first panel 51 in order to place through winding pins, and each separation panel 58–61 comprises a row of respective elongated holes 71 aligned with the row of holes 70 of the first panel 51 after the separation panel has been folded back.

Above the area arranged above the separation panels 58–61 and not covered by the backfolded second panel 52, there is a needle supporting means 24a in the form of a transverse strip of foam material whereto needles can be fixed.

Furthermore, locking elements in the form of slots 66 and tabs 65 are provided to lock the separation panels 60,61 in the closed state thereof. Further locking means in the form of transverse slots 67 and slots 68 in the shape of an inverted V are provided to lock the separation panels 58,59 in the closed state thereof.

Finally, locking elements in the form of transverse slots 69 are provided on the second panel 52 interlocking with the slots 68 of the first panel 51 after closing in order to secure the second panel 52 in the closed state thereof.

The second panel 52 is provided with two transverse rows of longitudinal elongated holes 72 arranged to align with the holes 70,71. Thereby it is possible to close the second panel 52, while the sewing material carrier 45 is still located on the winding pins. The first panel 51 comprises a tab 73, which can be folded back, so that the sewing material carrier 45 having the same format can be extracted from the envelope of the package.

The sewing material carrier 45 differs from the package represented in FIG. 1, especially in that it does not comprise any closing panels 34,35. The individual thread coils are produced and covered by the separation panels in the sewing material carrier in the same manner as in the package. FIG. 11 shows the sewing material carrier ready to close, shortly before the second panel 52 is folded back onto the separation panels 58,59 lying on top. The needles 43 are secured to the needle supporting means 24a and are exposed to be extracted. When a needle 43 is extracted, the corresponding thread follows without becoming entangled with other threads.

FIGS. 12–18 show a further package 80 for surgical sewing material. This provides a carton blank with a first panel 81 connected to a second panel 82 by a folding line and to a cover panel 83 by a further folding line running parallel thereto. The panels 81,82,83 are arranged behind each other in a longitudinal direction. Arranged at each side of the first panel 81 is a separation panel 84 and 85, respectively, which can cover half the width of the first panel 81 in the backfolded state. A backfolding panel 86 and 87, respectively, borders on each separation panel 84.

Figure 15:
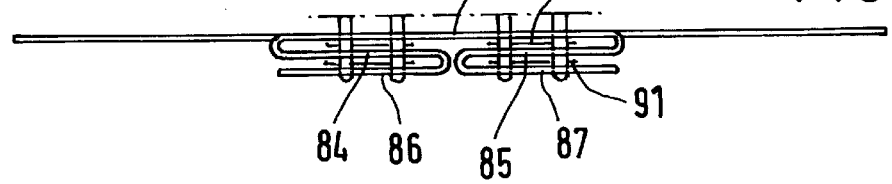
FIG. 15 shows the backfolding panel being folded over.
Figure 16:
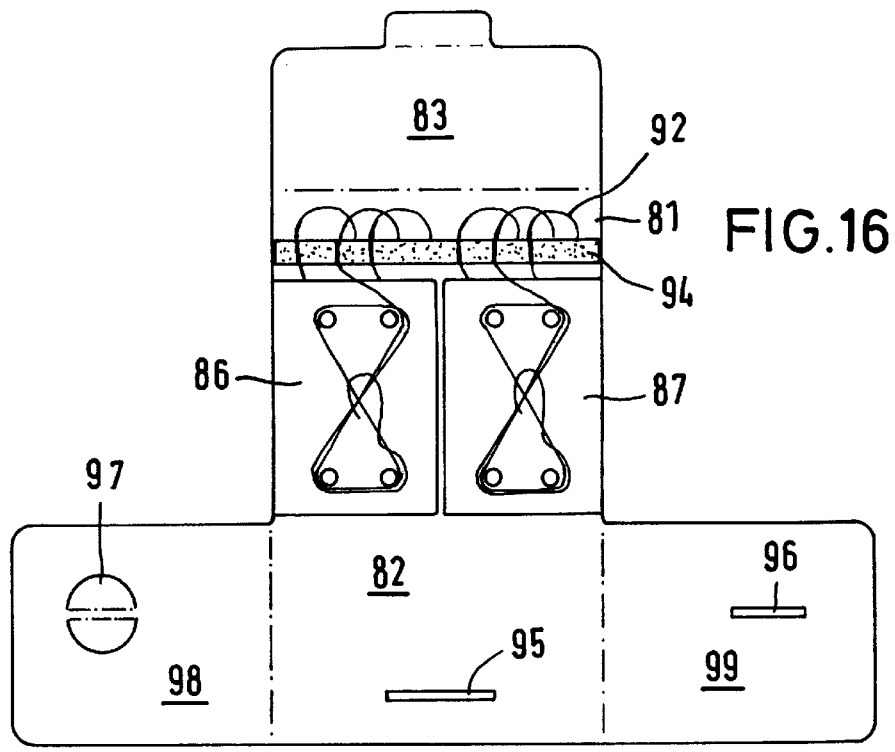
FIG. 16 shows a representation of the package according to FIG. 12 after the thread coils have been produced and covered.
Figure 17:
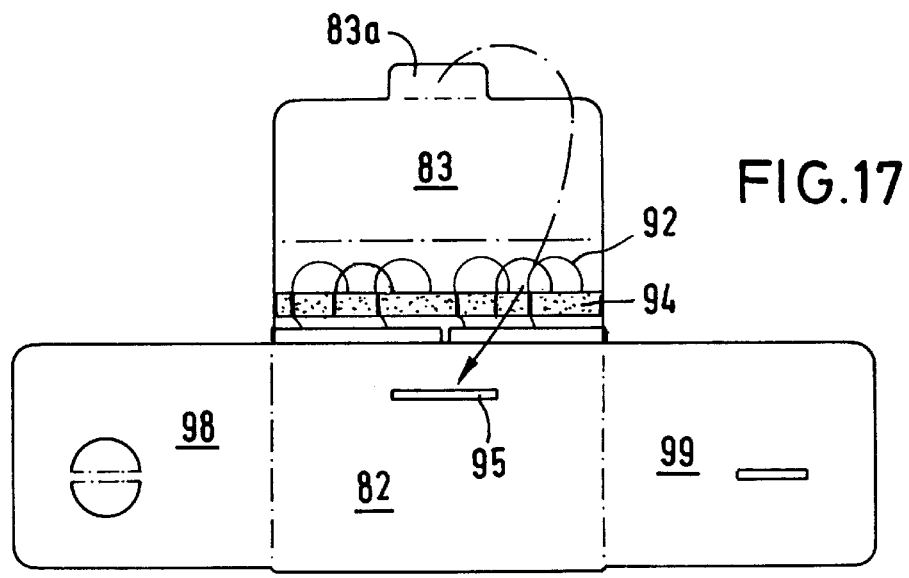
FIG. 17 shows the package according to FIG. 16 being closed.

Holes 88 are provided in the first panel 81, wherethrough winding pins 90 can be placed to form a thread coil 91 out of the sewing material. One or two needle(s) 92 are secured to the sewing material carrier 94 consisting of foam material. After two thread coils 91 have been formed on the left half and the right half of the first panel 81, the separation panels 84 and 85 are folded back (FIG. 14), and further thread coils 91 can be wound on the back sides of the separation panels 84,85 (FIG. 15). Then the backfolding panels 86,87 are folded back over the respective separation panel 84,85 (FIG. 15), thereby completely covering and securing these thread coils. This state is also shown in FIG. 16; additional sewing material coils can be placed on the backfolding panel 86,87.

Figure 14:
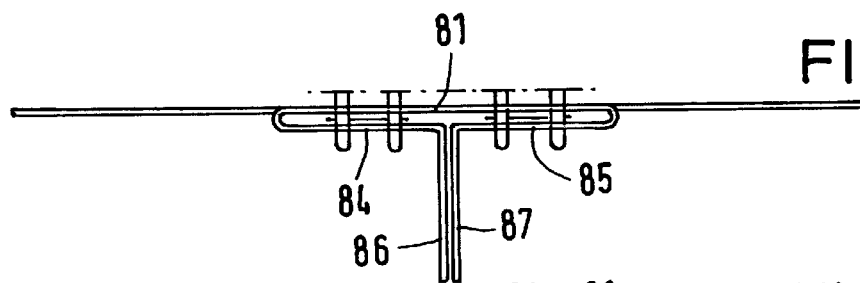
FIG. 14 shows the separation panels being folded over.

It is not necessary for the backfolding panels 86,87 to stand off rectangularly, as shown in FIG. 14, while the thread coils 91 are being wound on the separation panels 84,85. Each separation panel 86,87 can also lie flat while the coil is being wound, and then be folded back by 180°.

Figure 18:
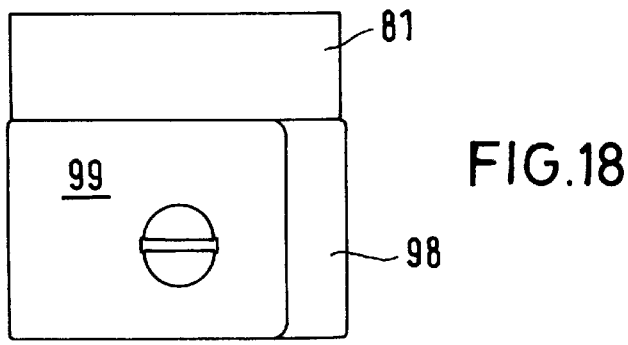
FIG. 18 shows a back view of the closed package according to FIG. 17.

The second panel 82 laterally borders on two closing panels 98,99 comprising cooperative closing parts 96,97. When the second panel 82 is folded over the backfolding panels 86,87 (FIG. 17), the closing panels 98,99 are folded around the lateral edges of the first panel and locked on the back side of the first panel with the closing parts 96,97 thereof. FIG. 18 shows the back view of the closed package 90. The cover panels 83 are folded down over the front side of the first panel 81 and locked with the tab 83a thereof in a slot 95 of the second panel 82. Thus, the cover panel 83 covers the needle supporting means 94 with the needles secured thereto.

In order to extract sewing material, the cover panel 83 is folded out. Thereby the needles 92 are exposed to be extracted, and the individual threads can be pulled out by pulling on the corresponding needle 92.

In the case of the package 90, it is also possible to insert a separate sewing material carrier into the envelope formed by the package, thus forming multiple layers of sewing material set off above each other or behind each other.

In the embodiment of FIGS. 19–22, there is provided a sewing material carrier 100 housed in an envelope 101. The sewing material carrier 100 forms a package containing the sewing material. It comprises a first panel 111, which is trapezoid in shape in the present embodiment and tapers towards that terminal area where the needle supporting means 124 is arranged. Thus, the width of the first panel 111 decreases from the lower part towards the upper part. Separation panels are pivoted to the two slant lateral edges, only the upper separation panels 120,121 thereof being visible in FIG. 19, which have been folded over the first panel 111 from the right. Below the separation panels 120,121, there are the separation panels 120a and 121a pivoted to the left, which are covered by the separation panels 120,121. Each of the separation panels only extends across half the height of the area of the thread coils to be covered. Additionally, a further cover panel 112 can be provided.

Figure 19:
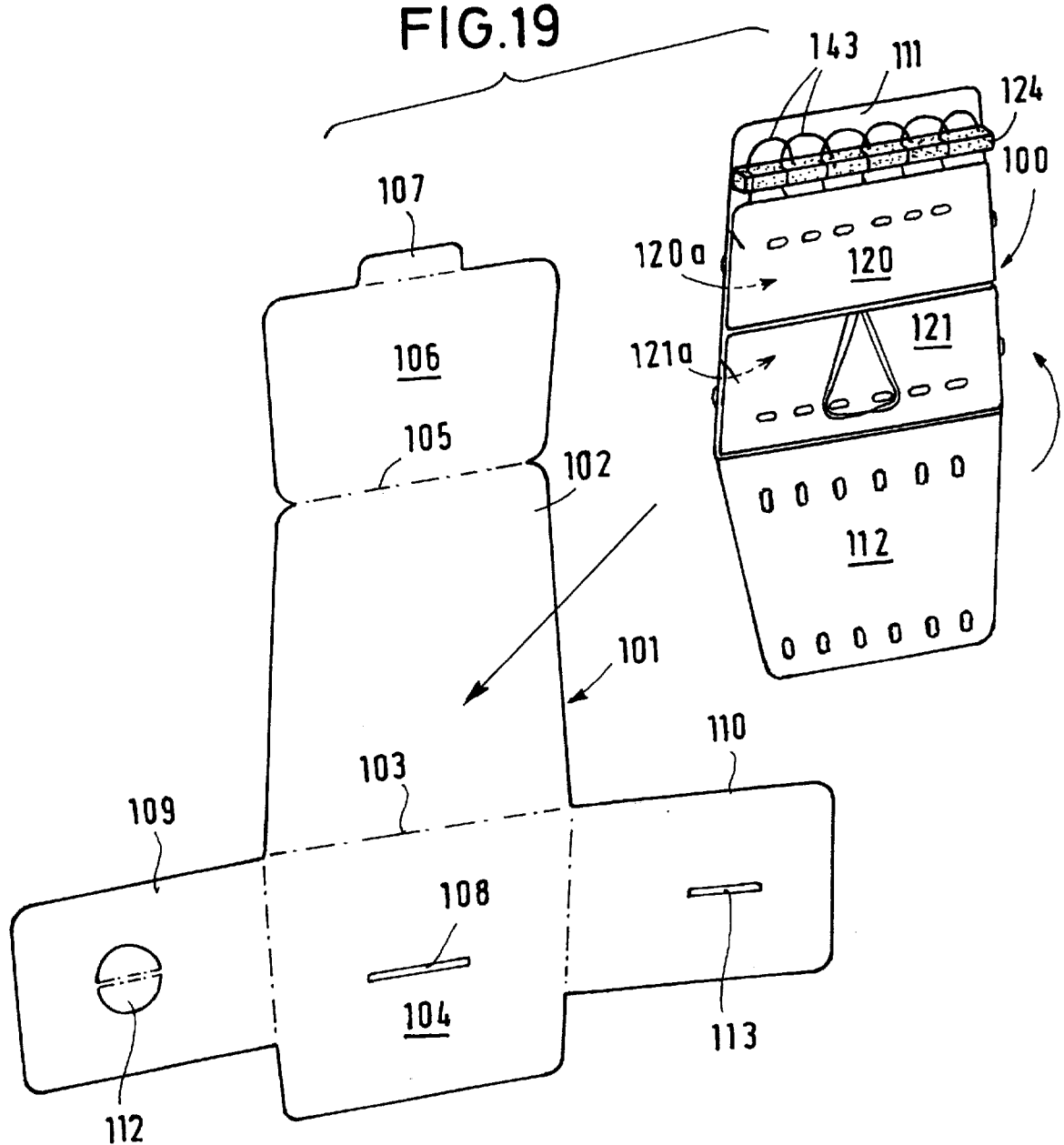
FIG. 19 shows a sewing material carrier being inserted into a separate envelope being shown in an unfolded state.

The envelope 101, represented in a state of being folded apart in FIG. 19, comprises a base panel 102 substantially congruent to the first panel 111 of the sewing material carrier 100 and having a trapezoid shape as well. The broad side of the trapezoid shape borders on a cover panel 104 by a folding line 103, which cover panel is able to cover the separation panel 120,121, with the needle supporting means 124 remaining exposed. The cover panel 106 is pivoted to the opposite end of the base panel 102 by a folding line 105, the cover panel being provided with a tab 107 insertable into a slot 108 of the cover panel 104. Closing panels 109,110 project into opposite directions from the two sides of the cover panels 104. The closing panels comprise engaging closing elements 112,113 by means of which they can interlock on the back side of the base panel 102.

FIG. 22 shows the sewing material carrier 100 placed fittingly on the base panel 102 of the envelope 101, the cover panel 104 being folded over the separation panels so that these are no longer visible. The needle supporting means 124, however, is left exposed by the cover panel 104. The closing panels 109,110 are folded over each other behind the base panel 102 and locked by means of the locking elements 112,113. Then the cover panel 106 is folded over the cover panel 104, the tab 107 being inserted into the slot 108.

FIG. 21 shows the envelope 101 in the closed state, and FIG. 22 shows the envelope 101, after the cover panel has been folded up, in a state in which the needle 143 with the threads attached thereto can be taken out. It can further be seen that the needle supporting means 124 is exposed and that the needle material carrier 100 cannot be extracted from the envelope 101, as the envelope opening 114 has a smaller width, because of the trapezoid shape of the envelope 101, than the part of the envelope located below and the sewing material carrier 100 thereof. Thus, the sewing material carrier 100 cannot be extracted from the envelope 101.

Another possibility of securing the sewing material carrier in the envelope would consist in securing the back side of the first panel 111 to the base panel of the envelope, for example by adhesive points.

The described embodiments each show needle supporting means 24,24a,94 consisting of a horizontal strip of foam material. It may be suitable to replace the horizontal strip of foam material by multiple longitudinal vertical strips of foam material with spaces between each other into which the needles can be inserted.

Although preferred embodiments of the invention have been specifically illustrated and described herein, it is to be understood that minor variations may be made without departing from the spirit and scope of the invention as defined in the appended claims.

I claim:

1. A multithread package for surgical sewing material comprising surgical sewing material including at least a first and second needle (43) and a respective first and second thread (42), a first panel (11; 51; 81; 111), separation panels (18–21; 58–61; 84, 85; 120, 121; 120a, 121a) foldably connected by fold lines at two opposite edges of said first panel (11; 51; 111), one of said separation panels (19) lying over said at least first thread (42) of said sewing material and also lying under said at least second thread (42), and said first panel (11; 51; 81; 111) supports a needle supporting means (24; 24a; 94; 124), not covered by said separation panels folded over said first panel, for supporting said at least first and second needles (43).

2. The multithread package as defined in claim 1 wherein said one separation panel (19) and a second separation panel (21) opposite each other are folded over each other on said first panel (11; 51; 81;111).

3. The multithread package as defined in claim 1 wherein two opposite separation panels (84, 85) each only extend across a part of said first panel (81) and are connected to corresponding backfolding panels (86, 87).

4. The multithread package as defined in claim 1 wherein said separation panels (18–21; 58–61; 120, 121; 120a, 121a) include holes 41; 71; 89) superimposed over holes (40; 70; 88) of said first panel in the relatively folded positions thereof.

5. The multithread package as defined in claim 4 wherein said holes (47; 71; 89) of at least one of said separation and cover panels are at least as large as the holes (40, 70, 88) of said first panel.

6. The multithread package as defined in claim 1 wherein a second panel (12; 52; 82, 112) is connected to said first panel (11; 51; 81, 111) adjacent an edge opposite said needle supporting means (24; 24a; 94, 124) and leaves exposed said needle supporting means (24; 24a; 94, 124) when said second panel is folded over said first panel.

7. The multithread package as defined in claim 6 wherein said second panel (12; 82) is connected at opposite edges thereof to closing panels (34, 35; 98, 99) which when folded over are superimposed over an outer side of said first panel and include cooperative locking elements (36, 37; 98, 99), and the first and second panels being enclosed by an envelope (48).

8. The multithread package as defined in claim 7 wherein the envelope (48) comprises an extractable separate sewing material carrier (45) with lateral and covering panels.

9. The multithread package as defined in claim 8 wherein the sewing material carrier (45) comprises a needle supporting means (24a) and does not cover the needle supporting means (24) of the first panel (11, 81), and the second panel (12, 82) leaves exposed the needle supporting means (24a) of the separate sewing material carrier (45) inserted into the envelope (48).

10. The multithread package as defined in claim 1 including a sewing material carrier (100) contained and secured in a separate envelope (101).

11. The multithread package as defined in claim 10 wherein the width of the envelope (101) and of the sewing material carrier (100) contained therein decreases towards an envelope opening (114) whereby the extraction of the sewing material carrier (100) out of the envelope opening (114) is avoided.

* * * * *